(12) United States Patent
Frangioni

(10) Patent No.: US 8,229,548 B2
(45) Date of Patent: Jul. 24, 2012

(54) MEDICAL IMAGING SYSTEMS

(75) Inventor: John V. Frangioni, Wayland, MA (US)

(73) Assignee: Beth Israel Deaconess Medical Center, Boston, MA (US)

(*) Notice: Subject to any disclaimer, the term of this patent is extended or adjusted under 35 U.S.C. 154(b) by 327 days.

(21) Appl. No.: 10/507,253

(22) PCT Filed: Mar. 11, 2003

(86) PCT No.: PCT/US03/07596
§ 371 (c)(1),
(2), (4) Date: Mar. 21, 2005

(87) PCT Pub. No.: WO03/077749
PCT Pub. Date: Sep. 25, 2003

(65) Prior Publication Data
US 2005/0182321 A1    Aug. 18, 2005

Related U.S. Application Data

(60) Provisional application No. 60/363,413, filed on Mar. 12, 2002.

(51) Int. Cl.
*A61B 6/00*    (2006.01)
(52) U.S. Cl. .................................. 600/473; 600/476
(58) Field of Classification Search .................. 600/433, 600/476, 473
See application file for complete search history.

(56) References Cited

U.S. PATENT DOCUMENTS

| | | | |
|---|---|---|---|
| 4,807,026 A | * | 2/1989 | Nishioka et al. ............... 348/70 |
| 4,821,117 A | * | 4/1989 | Sekiguchi .................... 348/68 |
| 5,079,662 A | | 1/1992 | Kawakami et al. |
| 5,120,953 A | | 6/1992 | Harris |

(Continued)

FOREIGN PATENT DOCUMENTS

WO    WO-2001050955 A1    7/2001

(Continued)

OTHER PUBLICATIONS

"U.S. Appl. No. 10/572,169, Non-Final Office Action mailed Apr. 29, 2009", 22 pgs.

(Continued)

*Primary Examiner* — Tse Chen
*Assistant Examiner* — Peter Luong
(74) *Attorney, Agent, or Firm* — Edwards Wildman Palmer LLP; Peter F. Corless

(57) ABSTRACT

A medical imaging system provides simultaneous rendering of visible light and fluorescent images. The system may employ dyes in a small-molecule form that remains in a subject's blood stream for several minutes, allowing real-time imaging of the subject's circulatory system superimposed upon a conventional, visible light image of the subject. The system may also employ dyes or other fluorescent substances associated with antibodies, antibody fragments, or ligands that accumulate within a region of diagnostic significance. In one embodiment, the system provides an excitation light source to excite the fluorescent substance and a visible light source for general illumination within the same optical guide that is used to capture images. In another embodiment, the system is configured for use in open surgical procedures by providing an operating area that is closed to ambient light. More broadly, the systems described herein may be used in imaging applications where a visible light image may be usefully supplemented by an image formed from fluorescent emissions from a fluorescent substance that marks areas of functional interest.

28 Claims, 4 Drawing Sheets

U.S. PATENT DOCUMENTS

| | | | |
|---|---|---|---|
| 5,187,572 A | | 2/1993 | Nakamura et al. |
| 5,255,087 A | | 10/1993 | Nakamura |
| 5,323,009 A | | 6/1994 | Harris |
| 5,526,814 A | | 6/1996 | Cline et al. |
| 5,582,576 A | * | 12/1996 | Hori et al. .................. 600/167 |
| 5,827,190 A | | 10/1998 | Palcic et al. |
| 5,851,181 A | * | 12/1998 | Talmor ........................ 600/407 |
| 5,954,650 A | * | 9/1999 | Saito et al. ................... 600/425 |
| 6,018,565 A | | 1/2000 | Ergun et al. |
| 6,061,591 A | * | 5/2000 | Freitag et al. ................ 600/476 |
| 6,099,466 A | * | 8/2000 | Sano et al. .................... 600/160 |
| 6,167,297 A | * | 12/2000 | Benaron ....................... 600/431 |
| 6,192,269 B1 | | 2/2001 | Okumura et al. |
| 6,212,425 B1 | | 4/2001 | Irion et al. |
| 6,284,223 B1 | * | 9/2001 | Luiken ........................ 424/9.6 |
| 6,289,236 B1 | * | 9/2001 | Koenig et al. ................ 600/477 |
| 6,293,911 B1 | * | 9/2001 | Imaizumi et al. ............. 600/160 |
| 6,334,847 B1 | * | 1/2002 | Fenster et al. ................ 600/443 |
| 6,671,540 B1 | * | 12/2003 | Hochman ..................... 600/431 |
| 6,775,565 B1 | | 8/2004 | Wieringa |
| 6,804,549 B2 | * | 10/2004 | Hayashi ....................... 600/431 |
| 6,898,458 B2 | * | 5/2005 | Zeng et al. ................... 600/476 |
| 6,915,154 B1 | | 7/2005 | Docherty et al. |
| 2001/0007920 A1 | | 7/2001 | Hayashi |
| 2002/0090119 A1 | * | 7/2002 | Saito et al. ................... 382/128 |
| 2003/0078477 A1 | * | 4/2003 | Kang et al. ................... 600/178 |
| 2003/0187319 A1 | * | 10/2003 | Kaneko et al. ................... 600/9 |
| 2004/0245350 A1 | | 12/2004 | Zeng |
| 2005/0065430 A1 | | 3/2005 | Wiethoff et al. |
| 2005/0182321 A1 | | 8/2005 | Frangioni |

FOREIGN PATENT DOCUMENTS

| | | |
|---|---|---|
| WO | WO-2005/0079662 A1 | 9/2005 |
| WO | WO-2008042486 A2 | 4/2008 |

OTHER PUBLICATIONS

Intl. Searching Authority, "International Search Report", for US Patent App No. PCT/US03/07596, Aug. 4, 2005.

"U.S. Appl. No. 10/572,169, Final Office Action mailed Jan. 20, 2010", , 20.

"U.S. Appl. No. PCT/US03/29368", *PCT Search Report* mailed Oct. 23, 2003, all.

* cited by examiner

MEDICAL IMAGING SYSTEMS

CROSS-REFERENCE TO RELATED APPLICATIONS

This application is a national stage filing under 35 U.S.C. 371 of International Application PCT/US03/07596, filed Mar. 11, 2003, which claims priority from U.S. Application No. 60/363,413, filed Mar. 12, 2002, the specification of which is hereby incorporated by reference in their entirety. International Application PCT/US03/07596 was published under PCT Article 21(2) in English.

GOVERNMENT INTERESTS

The United States Government has certain rights in this invention pursuant to National Institute of Health Grant # R21CA88245 and Department of Energy Grant # DE-FG02-01ER63188.

BACKGROUND OF THE INVENTION

Absorption and fluorescent dyes, such as indocyanine green, have proven useful for medical imaging applications. Some of the more commonly used dyes share a number of useful characteristics. First, the dyes are suitable for labeling antibodies or low-molecular-weight ligands of diagnostic significance, or otherwise adapted for sequestration or preferential uptake at a site of interest such as a lesion. The dyes are safe for injection or other introduction into a live subject. And finally, the dyes emit light at a specific wavelength when excited, so that their location and concentration may be tracked.

A number of imaging systems have been devised to detect and display these dyes within living tissue. For example, dyes such as indocyanine green have been used to visualize blood flow in eyes. In some cases, such as U.S. Pat. No. 6,293,911 to Imaizumi et al., a dye imaging device has been combined with a visible light imaging system. Imaizumi describes endoscopic tools that generate images of dye-labeled antibodies superimposed over visible light images captured from within the body. As a significant disadvantage, the Imaizumi system employs a number of separate cavities within an endoscopic tool for light sources and image capture, thus requiring a greater cross-sectional area for the endoscope. As a further disadvantage, the Imaizumi patent only discloses endoscopic applications, and may not be suitable for use in open surgical applications where ambient light may extend into the excitation and/or emission wavelengths of the dye.

There remains a need for improved surgical and diagnostic imaging tools capable of generating circulatory blood flow images or other functional images along with visible light images of a subject.

SUMMARY OF THE INVENTION

A medical imaging system provides simultaneous rendering of visible light and fluorescent images. The system may employ dyes in a small-molecule form that remains in a subject's blood stream for several minutes, allowing real-time imaging of the subject's circulatory system superimposed upon a conventional, visible light image of the subject. The system may also employ dyes or other fluorescent substances associated with antibodies, antibody fragments, or ligands that accumulate within a region of diagnostic significance. In one embodiment, the system provides an excitation light source to excite the fluorescent substance and a visible light source for general illumination within the same optical guide that is used to capture images. In another embodiment, the system is configured for use in open surgical procedures by providing an operating area that is closed to ambient light. More broadly, the systems described herein may be used in imaging applications where a visible light image may be usefully supplemented by an image formed from fluorescent emissions from a fluorescent substance that marks areas of functional interest.

The medical imaging system may include a visible light source providing light over a range of wavelengths that includes one or more wavelengths of visible light; an excitation light source providing light at one or more wavelengths outside the range of wavelengths of the visible light source, the one or more wavelengths selected to excite a fluorescent substance, which emits one or more photons at an emission wavelength; an electronic imaging device; an optical guide having a first end with a lens that captures an image of a subject and a second end that couples the image to the electronic imaging device; and a filter for coupling the visible light source and the excitation light source into the optical guide, the filter reflecting some of the light provided by the visible light source and some of the light from the excitation light source toward the subject, the filter further transmitting some visible light from the subject captured by the lens toward the electronic imaging device, and the filter further transmitting the emission wavelength from the subject captured by the lens toward the electronic imaging device.

In another embodiment, the system may include a visible light source illuminating a subject, the visible light source providing a range of wavelengths including one or more wavelengths of visible light; an excitation light source illuminating the subject, the excitation light source providing an excitation wavelength that is not one of the one or more wavelengths of visible light; a fluorescent substance introduced into a circulatory system of the subject, the fluorescent substance being soluble in blood carried by the circulatory system and the fluorescent substance emitting photons at an emission wavelength in response to the excitation wavelength; an electronic imaging device that captures an image of a field of view that includes some portion of the subject and the circulatory system of the subject, the image including a first image obtained from the one or more wavelengths of visible light and a second image obtained from the emission wavelength; and a display that renders the first image and the second image, the second image being displayed at a visible light wavelength.

In another embodiment, the system may include an operating area closed to ambient light, the operating area including a surgical field where a surgical procedure may be performed on a subject; a visible light source illuminating the surgical field, the visible light source providing a range of wavelengths including one or more wavelengths of visible light; an excitation light source illuminating the surgical field, the excitation light source including at least one wavelength outside the range of wavelengths of visible light; a fluorescent substance suitable for in vivo use, the fluorescent substance fluorescing at an emission wavelength in response to the at least one wavelength of the excitation light source, the fluorescent substance being introduced into the surgical field; an electronic imaging device that captures a visible light image of the surgical field and an emission wavelength image of the surgical field; and a display that renders the visible light image and the emission wavelength image of the surgical field, the emission wavelength image being displayed at a visible light wavelength.

In another embodiment, the system may include a visible light source that illuminates a subject, the visible light source providing a range of wavelengths including one or more wavelengths of visible light; an excitation light source that illuminates the subject at the same time that the visible light source illuminates the subject, the excitation light source providing an excitation wavelength that is not one of the one or more wavelengths of visible light; a fluorescent substance introduced into a circulatory system of the subject, the fluorescent substance being soluble in blood carried by the circulatory system and the fluorescent substance emitting photons at an emission wavelength in response to the excitation wavelength; and an electronic imaging device that captures an image of a field of view that includes some portion of the subject and the circulatory system of the subject, the image including a first image obtained from the one or more wavelengths of visible light and a second image concurrently obtained from the emission wavelength.

In the embodiments above, the one or more wavelengths of visible light from the visible light source may exclude far-red light, at least one of the excitation light source and the emission wavelength including a far-red light wavelength. The filter may be a dichroic mirror placed in the optical guide at a forty-five degree angle to a central axis of the optical guide.

The system may include a second filter. The second filter may separate the emission wavelength from the range of wavelengths from the visible light source, the emission wavelength being directed toward a first optical transducer of the electronic imaging device and the range of wavelengths from the visible light source being directed toward a second optical transducer of the electronic imaging device. The second filter may separate the emission wavelength from the range of wavelengths from the visible light source, the emission wavelength being directed toward a first optical transducer of the electronic imaging device and the range of wavelengths from the visible light source being directed toward a second optical transducer of the electronic imaging device wherein the second optical transducer separately senses at least each one of red, green, and blue light intensities. The second filter may separate the emission wavelength from the range of wavelengths from the visible light source, the emission wavelength being directed toward a first optical transducer of the electronic imaging device and the range of wavelengths from the visible light source being directed toward a second optical transducer of the electronic imaging device wherein the second optical transducer separately senses at least each one of cyan, magenta, and yellow light intensities. The second filter may separate the emission wavelength from the range of wavelengths from the visible light source, the emission wavelength being directed toward a first optical transducer of the electronic imaging device and the range of wavelengths from the visible light source being directed toward a second optical transducer of the electronic imaging device wherein the second filter includes a dichroic mirror that reflects the emission wavelength and transmits the one or more wavelengths of visible light from the visible light source. The second filter may separate the emission wavelength from the range of wavelengths from the visible light source, the emission wavelength being directed toward a first optical transducer of the electronic imaging device and the range of wavelengths from the visible light source being directed toward a second optical transducer of the electronic imaging device wherein the second filter includes a dichroic mirror that reflects the one or more wavelengths of visible light from the visible light source and transmits the emission wavelength. The second filter may shape the wavelengths of the visible light source.

The electronic imaging device may include at least one charge-coupled device. The excitation light source may include a laser. The electronic imaging device may include a video camera sensitive to visible light. The electronic imaging device may include an emission wavelength camera. The electronic imaging device may capture a visible light image and an emission wavelength image, the system further including a processor that converts the emission wavelength image to a converted image having one or more visible light components, and combines the converted image with the visible light image for display. The electronic imaging device may capture a visible light image and an emission wavelength image, the system further including a processor that converts the emission wavelength image to a converted image having one or more visible light components, and superimposes the converted image onto the visible light image for display.

The electronic imaging device may capture a visible light image and an emission wavelength image, the visible light image being captured at thirty frames per second and the emission wavelength being captured at fifteen frames per second, the emission wavelength being converted to thirty frames per second for combination with the visible light image. The electronic imaging device may capture a visible light image and an emission wavelength image, wherein the visible light image is captured at thirty frames per second and the emission wavelength is captured at fifteen frames per second, the visible light image being converted to fifteen frames per second for combination with the emission wavelength image.

The system may include a display that displays images captured by the electronic imaging device. The display may be provided to a physician for use during a procedure, the procedure being at least one of a diagnostic procedure or a therapeutic procedure. The display may include a surgical microscope.

The fluorescent substance may label at least one of an antibody, an antibody fragment, or a low-molecular-weight ligand that accumulates at a lesion, the system being used to visualize the lesion. The fluorescent substance may be soluble in blood, the system being used to visualize a blood system. The display may render the second image of the circulatory system superimposed on the first image of the subject. The fluorescent substance may be a fluorescent dye injected into the subject by an intravenous injection. The fluorescent substance may be sprayed onto the subject. The fluorescent substance may be one or more quantum dots. The fluorescent substance may include at least one of indocyanine green; fluorescein; methylene blue, and IRDye78-CA.

The fluorescent substance may be a dye having a structure of the formula:

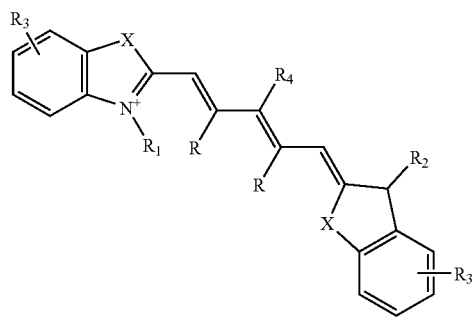

wherein, as valence and stability permit,

X represents $C(R)_2$, S, Se, O, or $NR_5$;

R represents H or lower alkyl, or two occurrences of R, taken together, form a ring together with the carbon atoms through which they are connected;

$R_1$ and $R_2$ represent, independently, substituted or unsubstituted lower alkyl, lower alkenyl, cycloalkyl, cycloalkylalkyl, aryl, or aralkyl;

$R_3$ represents, independently for each occurrence, one or more substituents to the ring to which it is attached;

$R_4$ represents H, halogen, or a substituted or unsubstituted ether or thioether of phenol or thiophenol; and $R_5$ represents, independently for each occurrence, substituted or unsubstituted lower alkyl, cycloalkyl, cycloalkylalkyl, aryl, or aralkyl.

A method as described herein may include illuminating a subject with one or more wavelengths of visible light; concurrently illuminating the subject with an excitation wavelength that is not one of the one or more wavelengths of visible light; introducing a fluorescent substance into a circulatory system of the subject, the fluorescent substance being soluble in blood carried by the circulatory system and the fluorescent substance emitting photons at an emission wavelength in response to the excitation wavelength; electronically capturing a visible light image of the subject; electronically capturing an emission wavelength image of the subject that shows the circulatory system; and displaying concurrently the visible light image of the subject and the emission wavelength image of the circulatory system.

In another embodiment, a method as described herein may include: enclosing a subject in an operating area closed to ambient light; illuminating the subject with one or more wavelengths of visible light; concurrently illuminating the subject with an excitation wavelength that is not one of the one or more wavelengths of visible light; introducing a fluorescent substance into the subject, the fluorescent substance emitting photons at an emission wavelength in response to the excitation wavelength; electronically capturing a visible light image of the subject; electronically capturing an emission wavelength image of the subject; and displaying concurrently the visible light image and the emission wavelength.

In another embodiment, a method described herein may include: providing one or more wavelengths of visible light; providing an excitation wavelength that is not one of the one or more wavelengths of visible light; introducing a fluorescent substance into a subject, the fluorescent substance emitting photons at an emission wavelength in response to the excitation wavelength; providing a laparoscope having a first optical path that directs the one or more wavelengths of visible light toward a subject, a second optical path that directs the excitation wavelength toward the subject, and a third optical path that directs an emission wavelength and the one or more wavelengths of visible light from the subject to an imaging device; making an incision in a body that includes the subject; directing the laparoscope into the incision so that the subject is within a field of view of the laparoscope; and displaying concurrently a visible light image of the subject and the emission wavelength image of the subject. At least two of the first optical path, the second optical path, and the third optical path may be coaxial.

In another embodiment, a method described herein may include: providing one or more wavelengths of visible light; providing an excitation wavelength that is not one of the one or more wavelengths of visible light; introducing a fluorescent substance into a subject, the fluorescent substance emitting photons at an emission wavelength in response to the excitation wavelength; providing an endoscope having an optical path for directing images of the subject to an imaging device; coupling the excitation wavelength and the one or more wavelengths of visible light into the optical path; directing the endoscope into a body so that the subject is within a field of view of the endoscope; capturing an emission wavelength image of the subject and a visible light image of the subject at the imaging device; and displaying concurrently the visible light image of the subject and the emission wavelength image of the subject.

The fluorescent substance may be a dye having a structure of the formula:

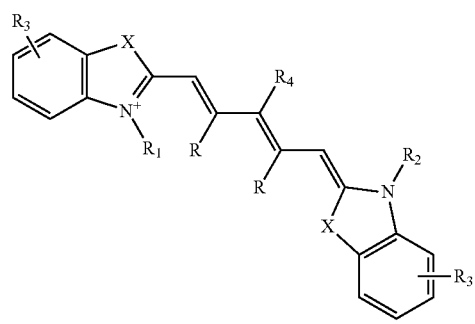

wherein, as valence and stability permit,

X represents $C(R)_2$, S, Se, O, or $NR_5$;

R represents H or lower alkyl, or two occurrences of R, taken together, form a ring together with the carbon atoms through which they are connected;

$R_1$ and $R_2$ represent, independently, substituted or unsubstituted lower alkyl, lower alkenyl, cycloalkyl, cycloalkylalkyl, aryl, or aralkyl;

$R_3$ represents, independently for each occurrence, one or more substituents to the ring to which it is attached;

$R_4$ represents H, halogen, or a substituted or unsubstituted ether or thioether of phenol or thiophenol; and $R_5$ represents, independently for each occurrence, substituted or unsubstituted lower alkyl, cycloalkyl, cycloalkylalkyl, aryl, or aralkyl.

BRIEF DESCRIPTION OF DRAWINGS

The invention will be appreciated more fully from the following further description thereof, with reference to the accompanying drawings, wherein.

DETAILED DESCRIPTION OF CERTAIN EMBODIMENTS OF THE INVENTION

To provide an overall understanding of the invention, certain illustrative embodiments will now be described, including a system for generating superimposed circulatory and tissue images in video format. However, it will be understood that the methods and systems described herein can be suitably adapted to other medical imaging applications where visible light tissue images may be usefully displayed with diagnostic image information obtained from outside the visible light range and superimposed onto the visible light image. More generally, the methods and systems described herein may be adapted to any imaging application where a visible light image may be usefully displayed with a superimposed image captured from areas within the visible light image that are functionally marked to emit photons outside the visible light range by a dye or other material. For example, the systems and methods are applicable to a wide range of diagnostic or surgical applications where a target pathology, tissue type, or cell may be labeled with a fluorescent dye or other fluorescent substance. These and other applications of the systems described herein are intended to fall within the scope of the invention.

Figure 1:
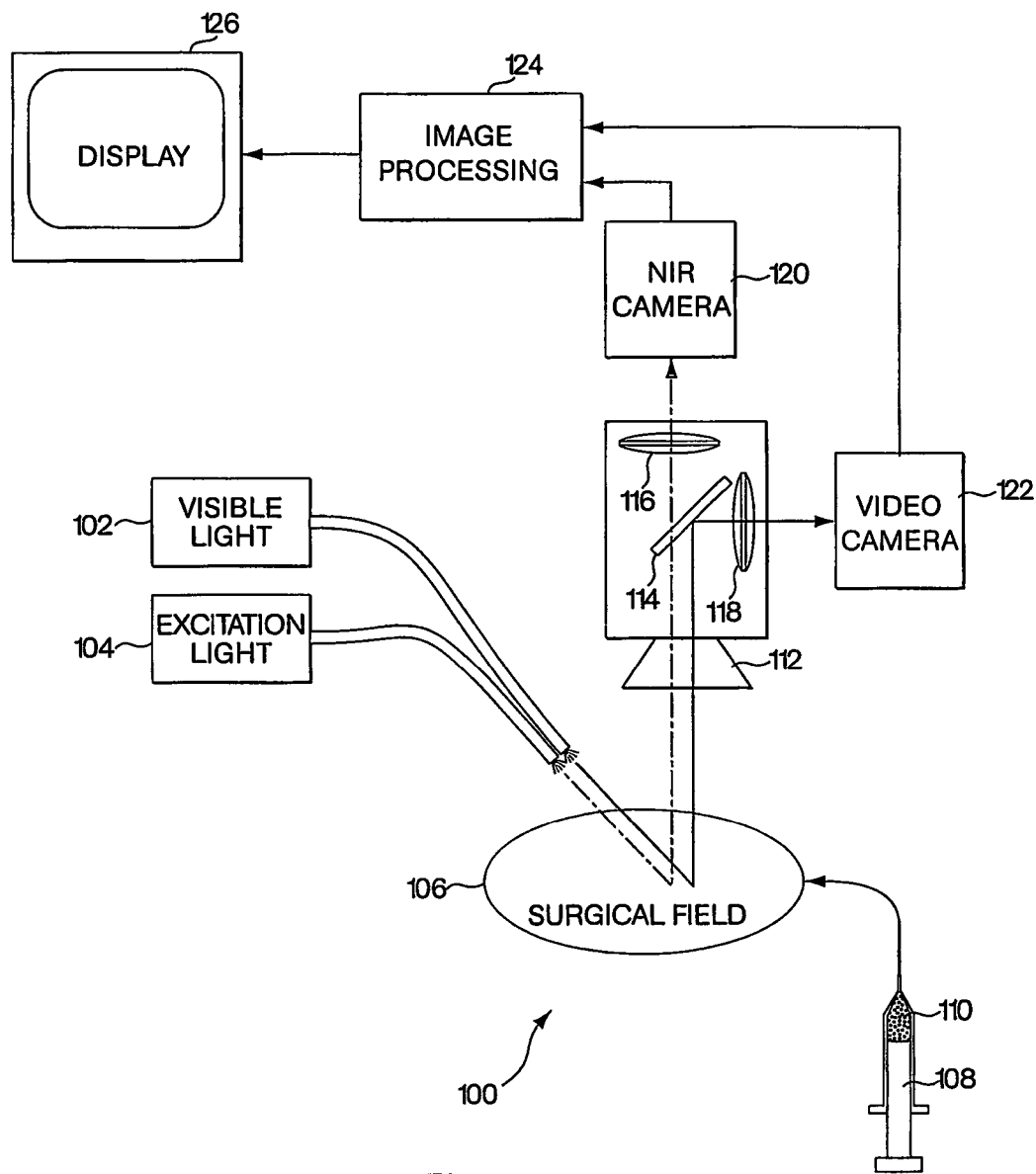
FIG. 1 shows an embodiment of an imaging system for use during open surgery.

FIG. 1 shows an embodiment of an imaging system for use during open surgery. The imaging system 100 may include a visible light source 102, and excitation light source 104, a surgical field 106, a dye source 108 containing a dye 110, a lens 112, a first filter 114, a second filter 116, a third filter 118, a near-infrared camera 120, a video camera 122, an image processing unit 124, and a display 126. In general, the visible light source 102 and the excitation light source 104 illuminate the surgical field 106. The dye 110 may be introduced from the dye source 108, such as through injection into the bloodstream of a subject. An image from the surgical field 106 is then captured by two cameras, the video camera 122 capturing a conventional, visible light image of the surgical field 106 and the near-infrared camera 120 capturing a diagnostic image based upon the distribution of the dye 110 in the surgical field 106. These images may be combined by the image processing unit 124 and presented on a display 126 where they may be used, for example, by a surgeon conducting a surgical procedure. Each aspect of the system 100 is now described in more detail.

The imaging system 100 may be surrounded by an operating area (not shown) closed to ambient light. As will become clear from the following, many visible light sources such as incandescent lamps, halogen lamps, or daylight may include a broad spectrum of electromagnetic radiation that extends beyond the range of visible light detected by the human eye and into wavelengths used in the present system as a separate optical channel for generating diagnostic images. In order to effectively detect emission in these super-visible light wavelengths, it is preferred to enclose the surgical field 106, light sources 102, 104, and cameras 120, 122 in an area that is not exposed to broadband light sources. This may be achieved by using an operating room closed to external light sources, or by using a hood or other enclosure or covering for the surgical field 106 that prevents invasion by unwanted spectrum. The visible light source 102 may then serve as a light source for the visible light camera 122, and also for provide conventional lighting within the visible light spectrum. As used herein, the term "operating area" is intended specifically to refer to an open surgical site that is closed to ambient light. Endoscopic or laparoscopic applications, as described below, are confined to surgical procedures within a closed body cavity, and do not include an operating area as that term is intended herein.

The visible light source 102 may be, for example, a near-infrared depleted white light source. This may be a one-hundred fifty Watt halogen lamp with one or more filters to deplete wavelengths greater than 700 nanometers ("nm"). Generally, any light source constrained to wavelengths between 400 nm and 700 nm may operate as the visible light source 102. In certain applications, the excitation light source 104 and resulting emission from the dye 110 may have wavelengths near or below 700 nm, as with Cy5 dye, which emits light when excited at 650 nm. These near-red dyes may be used with the present system, however, this requires a visible light source 102 that excludes a portion of the visible light spectrum in which the dye operates, i.e., a far-red depleted white light source. Similarly, applications using quantum dots as a fluorescent substance may have absorption or emission wavelengths anywhere in the visible light spectrum, and a suitable visible light source should be depleted at the wavelength(s) of interest. As such, the visible light source 102 should more generally be understood to be a source of light that includes some, but not necessarily all, of the wavelengths of visible light.

It should also be understood that, in a far-red imaging system or infrared imaging system such as those noted above, the near-infrared camera 120 described in the example embodiment will instead be a camera sensitive to the emission wavelength of the dye 110 or other fluorescent substance, and that other modifications to light sources, filters and other optics will be appropriate. Similar modifications may be made to isolate a band of wavelengths for dye excitation and emission anywhere within or outside the visible light range, provided that suitable optics, cameras, and dyes are available. Other fluorescent substances may also be used. For example, quantum dots may emit at visible light wavelengths, far-red, near-infrared, and infrared wavelengths, and at other wavelengths, typically in response to absorption below their emission wavelength. Suitable adjustments will be made to the excitation light source 104 and the emission camera, the near-infrared camera 120 in the example embodiment, for such applications. Cameras sensitive to far-red, near-infrared, and infrared wavelengths are commercially available.

The excitation light source 104 provides light at a wavelength that excites the dye 110. This may be, for example, a laser diode such as a 771 nm, 250 mW laser diode system, which may be obtained from Laser Components of Santa Rosa, Calif. Other single wavelength, narrowband, or broadband light sources may be used, provided they do not interfere with the visible light image captured by the video camera 122 or the emission wavelength of the dye 110. The near-infrared band is generally understood to include wavelengths between 700 nm and 1000 nm, and is a useful wavelength range for a number of readily available excitation light sources 104 and dyes 110 that may be used with the systems described herein. Suitable optical coupling and lenses may be provided to direct each of the visible light source 102 and the excitation light source 104 at an area of interest within the surgical field 106.

The surgical field 106 may be any area of a subject or patient that is open for a surgical procedure. This may be, for example, an open chest during a procedure such as a revascularization or cardiac gene therapy, where visualization of the circulatory system may improve identification of areas at risk for myocardial infarction. Blood flow visualization may permit an assessment of coronary arteries during a coronary artery bypass graft, or an assessment of blood flow and viability during introduction of genes for endothelial growth factor or fibroblast growth factor to induce neovascularization within ischemic regions of the heart. More generally, the surgical field 106 may include any areas of a patient's body, such as a region of the body that includes a tumor that is to be surgically removed, and that is amenable to visualization with fluourescent dyes, such as through the use of labeled antibodies.

The dye source 108 may be any instrument used for injection or other introduction of the dye 110 into a subject, such as a hypodermic needle or angiocath. Where, for example, the dye 110 is highly soluble in blood, the dye source 108 may be administered anywhere on the subject, and need not be near the surgical field 106. For example, it has been found that IRDye78-CA (the carboxylic acid form of IRDye78), when injected intravenously into a live laboratory rat, produced peak vasculature image strength of an open heart approximately 5-10 seconds after injection, and remained adequate for visualization for over one minute. In certain embodiments, the dye source 108 may not use injection. For example, the dye source 108 may spray or otherwise apply the dye 110 to an area of interest. Depending upon the type of dye and the imaging technique, the dye 110 may be delivered in a discrete dose, or may be continuously or intermittently applied and re-applied by the dye source 108.

The dye 110 may be any dye suitable for use in vivo and having excitation and emission wavelengths suitable for other components of the system 100. Typically, the dye 110 will be diluted to 25-50 μM for intravenous injection, such as with phosphate buffered saline, which may be supplemented with Cremophor EL (Sigma) and/or absolute ethanol. A number of suitable near-infrared dyes are described below.

'Acyl' refers to a group suitable for acylating a nitrogen atom to form an amide or carbamate, a carbon atom to form a ketone, a sulfur atom to form a thioester, or an oxygen atom to form an ester group, e.g., a hydrocarbon attached to a —C(=O)— moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The terms 'amine' and 'amino' are art-recognized and refer to both unsubstituted and substituted amines as well as ammonium salts, e.g., as can be represented by the general formula:

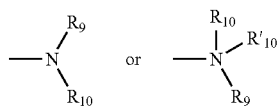

wherein $R_9$, $R_{10}$, and $R'_{10}$ each independently represent hydrogen or a hydrocarbon substituent, or $R_9$ and $R_{10}$ taken together with the N atom to which they are attached complete a heterocycle having from 4 to 8 atoms in the ring structure. In preferred embodiments, none of $R_9$, $R_{10}$, and $R'_{10}$ is acyl, e.g., $R_9$, $R_{10}$, and $R'_{10}$ are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., $R'_{10}$ is present) are referred to as 'ammonium' groups. In amino groups other than ammonium groups, the amine is preferably basic, e.g., its conjugate acid has a $pK_a$ above 7.

The terms 'amido' and 'amide' are art-recognized as an amino-substituted carbonyl, such as a moiety that can be represented by the general formula:

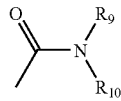

wherein $R_9$ and $R_{10}$ are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents.

Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heterocyclyl, and heteroaryl.

The terms 'alkenyl' and 'alkynyl' refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms 'alkoxyl' and 'alkoxy' as used herein refer to an —O-alkyl group. Representative alkoxyl groups include methoxy, ethoxy, propyloxy, tert-butoxy, and the like. An 'ether' is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl, —O-aralkyl, —O-heteroaralkyl, —O-carbocyclic aliphatic, or —O-heterocyclic aliphatic.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

'Cycloalkyl ring' refers to a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 4 to about 10 carbon atoms, preferably from 4 to 7 carbon atoms, and most preferably from 5 to 6 carbon atoms in the ring. Bicyclic cycloalkyl rings contain from 8 to 12 carbon atoms, preferably from 9 to 10 carbon atoms in the ring. Cycloalkyl rings may be unsubstituted or substituted with from 1 to 4 substituents on the ring. Preferred cycloalkyl ring substituents include halo, cyano, alkyl, heteroalkyl, haloalkyl, phenyl, phenoxy or any combination thereof. More preferred substituents include halo and haloalkyl. Preferred cycloalkyl rings include cyclopentyl, cyclohexyl, cyclohexenyl, cycloheptyl, and cyclooctyl. More preferred cycloalkyl rings include cyclohexyl, cycloheptyl, and cyclooctyl.

The term 'carbonyl' is art-recognized and includes such moieties as can be represented by the general formula:

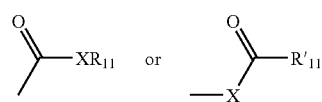

wherein X is a bond or represents an oxygen or a sulfur, and $R_{11}$ represents a hydrogen, hydrocarbon substituent, or a pharmaceutically acceptable salt, $R_{11'}$ represents a hydrogen or hydrocarbon substituent. Where X is an oxygen and $R_{11}$ or $R_{11'}$ is not hydrogen, the formula represents an 'ester'. Where X is an oxygen, and $R_{11}$ is as defined above, the moiety is referred to herein as a carboxyl group, and particularly when $R_{11}$ is a hydrogen, the formula represents a 'carboxylic acid'. Where X is an oxygen, and $R_{11'}$ is hydrogen, the formula represents a 'formate'. In general, where the oxygen atom of the above formula is replaced by sulfur, the formula represents a 'thiocarbonyl' group. Where X is a sulfur and $R_{11}$ or $R_{11'}$ is not hydrogen, the formula represents a 'thioester.' Where X is a sulfur and $R_{11}$ is hydrogen, the formula represents a 'thiocarboxylic acid.' Where X is a sulfur and $R_{11'}$ is hydrogen, the formula represents a 'thioformate.' On the other hand, where X is a bond, $R_{11}$ is not hydrogen, and the carbonyl is bound to a hydrocarbon, the above formula represents a 'ketone' group. Where X is a bond, $R_{11}$ is hydrogen, and the carbonyl is bound to a hydrocarbon, the above formula represents an 'aldehyde' or 'formyl' group.

'Ci alkyl' is an alkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substituents. Preferred halo are fluoro, chloro and bromo; more preferred are chloro and fluoro.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di-C1-C3 alkylamino, methylphenylamino, methylbenzylamino, C1-C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 4, preferably 1 to 3 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

'Member atom' refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

As used herein, the term 'nitro' means —NO$_2$.

'Pharmaceutically acceptable salt' refers to a cationic salt formed at any acidic (e.g., hydroxamic or carboxylic acid) group, or an anionic salt formed at any basic (e.g., amino or guanidino) group. Such salts are well known in the art. See e.g., World Patent Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The terms 'polycyclyl' and 'polycyclic group' refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed 'bridged' rings, and rings that are joined through adjacent atoms are 'fused rings'.

The term 'sulfate' is art-recognized and includes a moiety that can be represented by the general formula:

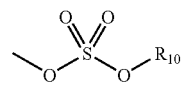

in which R$_{10}$ is as defined above.

A 'substitution' or 'substituent' on a small organic molecule generally refers to a position on a multivalent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986-87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and non-aromatic organic compounds which can be substituted or unsubstituted.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

In certain embodiments, the subject method employs a fluorescent dye having a structure of the formula:

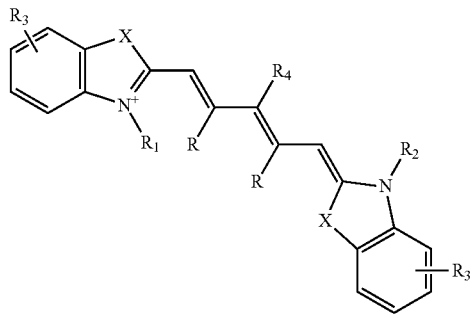

wherein, as valence and stability permit,

X represents $C(R)_2$, S, Se, O, or $NR_5$;

R represents H or lower alkyl, or two occurrences of R, taken together, form a ring together with the carbon atoms through which they are connected;

$R_1$ and $R_2$ represent, independently, substituted or unsubstituted lower alkyl, lower alkenyl, cycloalkyl, cycloalkylalkyl, aryl, or aralkyl, e.g., optionally substituted by sulfate, phosphate, sulfonate, phosphonate, halogen, hydroxyl, amino, cyano, nitro, carboxylic acid, amide, etc., or a pharmaceutically acceptable salt thereof;

$R_3$ represents, independently for each occurrence, one or more substituents to the ring to which it is attached, such as a fused ring (e.g., a benzo ring), sulfate, phosphate, sulfonate, phosphonate, halogen, lower alkyl, hydroxyl, amino, cyano, nitro, carboxylic acid, amide, etc., or a pharmaceutically acceptable salt thereof;

$R_4$ represents H, halogen, or a substituted or unsubstituted ether or thioether of phenol or thiophenol; and $R_5$ represents, independently for each occurrence, substituted or unsubstituted lower alkyl, cycloalkyl, cycloalkylalkyl, aryl, or aralkyl, e.g., optionally substituted by sulfate, phosphate, sulfonate, phosphonate, halogen, hydroxyl, amino, cyano, nitro, carboxylic acid, amide, etc., or a pharmaceutically acceptable salt thereof.

Dyes representative of this formula include indocyanine green, as well as:

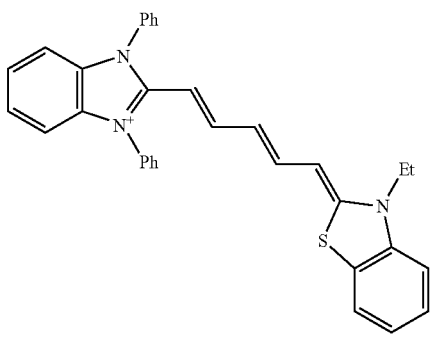

and

-continued

In certain embodiments wherein two occurrences of R taken together form a ring, the ring is six-membered, e.g., the fluorescent dye has a structure of formula:

wherein X, $R_1$, $R_2$, $R_3$, $R_4$, and $R_5$ represent substituents as described above.

Dyes representative of this formula include IRDye78, IRDye80, IRDye38, IRDye40, IRDye41, IRDye700, IRDye800, Cy7 (AP Biotech), and compounds formed by conjugating a second molecule to any such dye, e.g., a protein or nucleic acid conjugated to IRDye800, IRDye40, or Cy7, etc. The IRDyes are commercially available from Li-Cor Biosciences of Lincoln, Nebr., and each dye has a specified peak absorption wavelength (also referred to herein as the excitation wavelength) and peak emission wavelength that may be used to select suitable optical hardware for use therewith. It will be appreciated that other dyes may also be used, including the far-red dyes noted above, provided suitable adjustments are made to the visible light imaging components of the system 100, and other near-infrared dyes or infrared substances such as the previously mentioned quantum dots. Several specific dyes suited for specific imaging techniques are now described.

IRDye78-CA is useful for imaging the vasculature of the tissues and organs. The dye in its small molecule form is soluble in blood, and has an in vivo early half-life of several minutes. This permits multiple injections during a single procedure. Indocyanine green has similar characteristics, but is somewhat less soluble in blood and has a shorter half-life. IRDye78 may also be used in other imaging applications, since it can be conjugated to tumor-specific ligands for tumor visualization. More generally, IRDye78 may be linked to an antibody, antibody fragment, or ligand associated with a tumor. Presence of the tumor or lesion may then be visualized using the techniques described above.

As another example, IR-786 partitions efficiently into mitochondria and/or endoplasmic reticulum in a concentration-dependent manner, thus permitting blood flow and ischemia visualization in a living heart. The dye has been successfully applied, for example, to image blood flow in the heart of a living laboratory rat after a thoracotomy. More generally, IR-786 may be used for non-radioactive imaging of areas of ischemia in the living heart, or other visualization of the viability of other tissues.

While a number of suitable dyes have been described, it should be appreciated that such fluorescent dyes are examples only, and that more generally, any fluorescent substance may be used with the imaging systems described herein, provided the substance has an emission wavelength that does not interfere with visible light imaging. This includes the fluorescent dyes described above, as well as substances such as quantum dots which may have emission wavelengths above 1000 nm, and may be associated with an antibody, antibody fragment, or ligand and imaged in vivo. All such substances are referred to herein as fluorescent substances, and it will be understood that suitable modifications may be made to components of the imaging system for use with any such fluorescent substance.

The lens 112 may be any lens suitable for receiving light from the surgical field 106 and focusing the light for image capture by the near-infrared camera 120 and the video camera 122. The lens 112 may include one or more optical coatings suitable for the wavelengths to be imaged, and may provide for manual, electronically-assisted manual, or automatic control of zoom and focus.

The first filter 114 may be positioned in the image path from the lens 112 such that a visible light image having one or more visible light wavelengths is directed toward the video camera 122, either by reflection or transmittance. An emission image from the excited dye 110 passes through the lens 112 and is directed toward the near infrared camera 120, again either through reflection or transmittance. A number of arrangements of the cameras 120, 122 and the first filter 114 are possible, and may involving reflecting or transmitting either the visible light image or the emission wavelength image.

In one embodiment, IRDye78-CA (carboxylic acid) having a peak absorption near 771 nm and a peak emission near 806 nm, is used with the system 100. In this embodiment, the first filter 114 may be a 785 nm dichroic mirror that transmits near-infrared light and reflects visible light. The first filter 114 may be positioned within an image path from the lens 112 such that a visible light image of the surgical field 106 is reflected toward the video camera 122 through the third filter 118. The third filter 118 may be, for example, a 400 nm-700 nm visible light filter. At the same time, the first filter 114 is positioned with the image path from the lens 112 such that a near-infrared image (i.e., the excitation wavelength image) is transmitted toward the near-infrared camera 120 through the second filter 116. The second filter 116 may be an 810 nm+/− 20 nm near-infrared emission filter. The filters may be standard or custom-ordered optical components, which are commercially available from optical component suppliers. Other arrangements of filters and other optical components may be used with the system 100 described herein.

The near-infrared camera 120 may be any still or moving image camera suitable for capturing images at the emission wavelength of the excited dye 110. The near-infrared camera may be, for example, an Orca-ER near-infrared camera with settings of gain 7, 2×2 binning, 640×480 pixel field of view, and an exposure time of 20 msec and an effective frame rate of fifteen frames per second. The Orca-ER is commercially available from Hamamatsu Photonic Systems of Bridgewater, N.J. It will be understood that the near-infrared camera 120 of FIG. 1 is only an example. An infrared camera, a far-red camera, or some other camera or video device may be used to capture an emission wavelength image, with the camera and any associated filters selected according to the wavelength of a corresponding fluorescent substance used with the imaging system. As used herein, the term "emission wavelength camera" is intended to refer to any such camera that may be used with the systems described herein.

The video camera 122 may be any video camera suitable for capturing images of the surgical field 106 in the visible light spectrum. In one embodiment, the video camera 122 is a color video camera model HV-D27, commercially available from Hitachi of Tarrytown, N.Y. The video camera 122 may capture red-green-blue (RGB) images at thirty frames per second at a resolution of 640×480 pixels. More generally, the near-infrared camera 120 and the video camera 122 may be any device capable of photonic detection and conversion to electronic images, including linear photodiode arrays, charge coupled device arrays, scanning photomultiplier tubes, and so forth.

The display 126 may be a television, high-definition television, computer monitor, or other display configured to receive and render signals from the image processing unit 124. The surgical field 106 may also be a neurosurgical site, with a surgical microscope used to view the surgical field 106. In this embodiment, the display 126 may be a monocular or binocular eyepiece of the surgical microscope, with the near-infrared image superimposed on the visible light image in the eyepiece. In another embodiment, the eyepiece may use direct optical coupling of the surgical field 106 to the eyepiece for conventional microscopic viewing, with the near-infrared image projected onto the eyepiece using, for example, heads-up display technology.

The image processing unit 124 may include any software and/or hardware suitable for receiving images from the cameras 120, 122, processing the images as desired, and transmitting the images to the display 126. In one embodiment, the image processing unit 124 is realized in software on a Macintosh computer equipped with a Digi-16 Snapper frame grabber for the Orca-ER, commercially available from DataCell of North Billerica, Mass., and equipped with a CG-7 frame grabber for the HV-D27, commercially available from Scion of Frederick Md., and using IPLab software, commercially available from Sanalytics of Fairfax, Va. While a Macintosh may be used in one embodiment, any general purpose computer may be programmed to perform the image processing functions described herein, including an Intel processor-based computer, or a computer using hardware from Sun Microsystems, Silicon Graphics, or any other microprocessor manufacturer.

Generally, the image processing unit 124 should be capable of digital filtering, gain adjustment, color balancing, and any other conventional image processing functions. The image from the near-infrared camera 120 is also typically shifted into the visible light range for display at some prominent wavelength, e.g., a color distinct from the visible light colors of the surgical field 106, so that a superimposed image will clearly depict the dye. The image processing unit 124 may also perform image processing to combine the image from the near-infrared camera 120 and the video camera 122. Where the images are displayed side-by-side, this may simply entail rendering the images in suitable locations on a computer screen. Where the images are superimposed, a frame rate adjustment may be required. That is, if the video camera 122 is capturing images at the conventional rate of thirty frames per second and the near-infrared camera 120 is taking still pictures with an effective frame rate of fifteen frames per second, some additional processing may be required to render the superimposed images concurrently. This may entail either reducing the frame rate of the video camera 122 to the frame rate of the near-infrared camera 120 either by using every other frame of video data or averaging or otherwise interpolating video data to a slower frame rate. This may instead entail increasing the frame rate of the near-infrared image data, either by holding each frame of near-infrared data over successive frames of video data or extrapolating near-infrared data, such as by warping the near-infrared image according to changes in the video image or employing other known image processing techniques.

Generally, any combination of software or hardware may be used in the image processing unit 124. The functions of the image processing unit 124 may be realized, for example, in one or more microprocessors, microcontrollers, embedded microcontrollers, programmable digital signal processors or other programmable device, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The functions may also, or instead, include one or more application specific integrated circuits, programmable gate arrays, programmable array logic devices, or any other device or devices that may be configured to process electronic signals. Any combination of the above circuits and components, whether packaged discretely, as a chip, as a chipset, or as a die, may be suitably adapted to use with the systems described herein.

It will further be appreciated that each function of the image processing unit 124 may be realized as computer executable code created using a structured programming language such as C, an object-oriented programming language such as C++ or Java, or any other high-level or low-level programming language that may be compiled or interpreted to run on one of the above devices, as well as heterogeneous combinations of processors, processor architectures, or combinations of different hardware and software. The image processing unit 124 may be deployed using software technologies or development environments including a mix of software languages, such as Java, C++, Oracle databases, SQL, and so forth. It will be further appreciated that the functions of the image processing unit 124 may be realized in hardware, software, or some combination of these.

In one embodiment, the visible light source 102 is a near-infrared depleted visible light source, the excitation light source 104 is a 771 nm, 250 mW laser diode, the dye 110 is indocyanine green or IRDye78-CA, the first filter 114 is a 785 nm dichroic mirror configured to transmit near-infrared light and reflect visible light, the second filter 116 is an 810 nm+/−20 nm near-infrared emission filter, and the third filter 118 is a 400 nm to 700 nm filter. The image processing unit 124 is a computer with software for image capture from the near-infrared camera 120 and the video camera 122, for making suitable color adjustment to the images from the near-infrared camera 120, for making frame rate adjustments to the video camera 122 image, and for combining the two images for superimposed display on the display 126.

The systems described above have numerous surgical applications. For example, the system may be deployed as an aid to cardiac surgery, where it may be used intraoperatively for direct visualization of cardiac blood flow, for direct visualization of myocardium at risk for infarction, and for image-guided placement of gene therapy and other medicinals to areas of interest. The system may be deployed as an aid to oncological surgery, where it may be used for direct visualization of tumor cells in a surgical field or for image-guided placement of gene therapy and other medicinals to an area of interest. The system may be deployed as an aid to general surgery for direct visualization of any function amenable to imaging with fluorescent dyes, including blood flow and tissue viability. In dermatology, the system may be used for sensitive detection of malignant cells or other skin conditions, and for non-surgical diagnosis of dermatological diseases using near-infrared ligands and/or antibodies.

Figure 2:
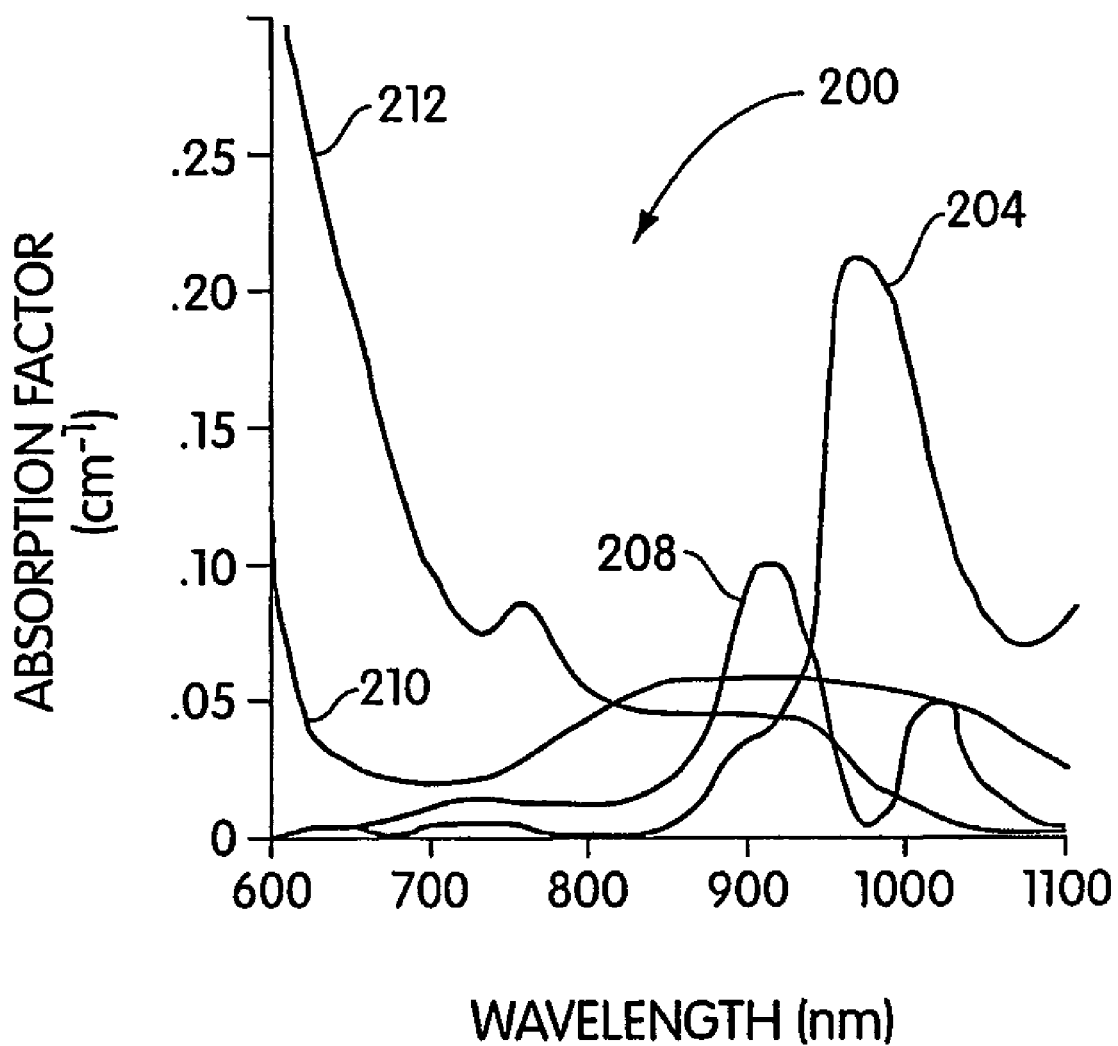
FIG. 2 shows a near-infrared window used by the imaging system.

FIG. 2 shows a near-infrared window used by the imaging system. The near-infrared window 200 is characterized by wavelengths where absorbance is at a minimum. The components of living tissue with significant near-infrared absorbance include water 204, lipid 208, oxygenated hemoglobin 210, and deoxygenated hemoglobin 212. As shown in FIG. 2, oxygenated hemoglobin 210 and deoxygenated hemoglobin have significant absorbance below 700 nm. By contrast, lipids 208 and water 204 have significant absorbance above 900 nm. Between 700 nm and 900 nm, these absorbances reach a cumulative minimum referred to as the near-infrared window 200. While use of excitation and emission wavelengths outside the near-infrared window 200 is possible, as described in some of the examples above, fluorescence imaging within the near-infrared window 200 offers several advantages including low tissue autofluorescence, minimized tissue scatter, and relatively deep penetration depths. While the near-infrared window 200 is one useful wavelength range for imaging, the systems described herein are not limited to either excitation or emission wavelengths in this window, and may employ, for example, far-red light wavelengths below the near-infrared window 200, or infrared light wavelengths above the near-infrared window 200, both of which may be captured using commercially available imaging equipment.

Figure 3:
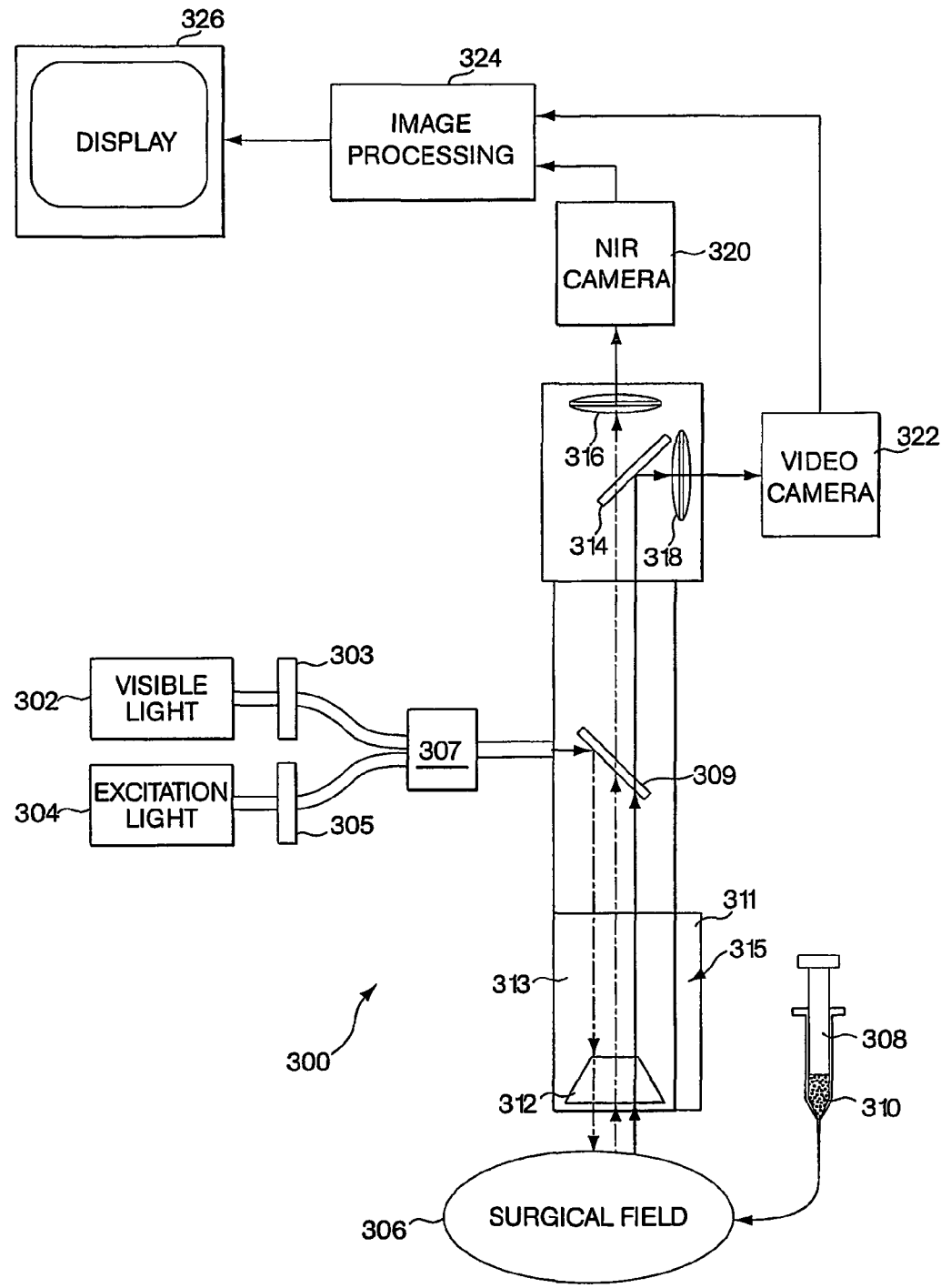
FIG. 3 shows an embodiment of an imaging system for use in an endoscopic tool.

FIG. 3 shows an embodiment of an imaging system for use in an endoscopic tool. The imaging system 300 may include a visible light source 302, and excitation light source 304, a surgical field 306, a dye source 308 containing a dye 310, a lens 312, a first filter 314, a second filter 316, a third filter 318, a near-infrared camera 320, a video camera 322, an image processing unit 324, and a display 326. In general, the visible light source 302 and the excitation light source 304 illuminate the surgical field 306. The dye 310 may be introduced from the dye source 308, such as through injection into the bloodstream of a subject. An image from the surgical field 306 is then captured by two cameras, the video camera 322 capturing a conventional, visible light image of the surgical field 306 and the near-infrared camera 320 capturing a diagnostic image based upon the distribution of the dye 310 in the surgical field 306. These images may be combined by the image processing unit 324 and presented on a display 326 where they may be used, for example, by a surgeon conducting a surgical procedure. In general, each of these components may be any of those components similarly described with reference to FIG. 1 above. Differences for an endoscopic tool are now described.

The imaging system 300 for use as an endoscopic tool may further include a first lens/collimator 303 for the visible light source, a second lens/collimator 305 for the excitation light source 304, an optical coupler 307 that combines the excitation light and the visible light, a dichroic mirror 309, and an endoscope 311 having a first cavity 313 and a second cavity 315.

The first lens/collimator 303, the second lens/collimator 305, and the optical coupler 307 serve to combine the excitation light and the visible light into a single light source. This light source is coupled into the first cavity 313 through the dichroic mirror 309. In one embodiment, the dichroic mirror 309 preferably provides fifty percent reflection of light having wavelengths from 400 nm to 700 nm, in order to optimize an intensity of visible light that reaches the video camera 322 after illuminating the surgical field 306 and passing through the dichroic mirror 309 on its return path to the video camera 322. The dichroic mirror 309 also preferably has greater than ninety percent reflection of wavelength from the excitation light source 304, such as between 700 nm and 785 nm, so that these wavelengths are not transmitted to the cameras 320, 322 after reflecting off the surgical field. Using this arrangement, visible and excitation light sources 302, 304 share the first cavity 313 of the endoscope with the return light path for a visible light image and an emission wavelength image.

The second cavity 315 of the endoscope 311 may be provided for insertion of a tool, such as an optical tool like a laser for irradiation of a site in the surgical field 306, or a physical tool like an instrument for taking a biopsy of tissue within the surgical field. By combining the optical paths of the imaging system 300 within a single cavity of the endoscope 311, the combined gauge of the first cavity 313 for imaging and the second cavity 315 may be advantageously reduced.

The imaging system 300 may instead be used with a laparoscope. Typically, a laparoscope is inserted into a body cavity through an incision, as distinguished from an endoscope which is inserted through an existing body opening such as the throat or rectum. A laparoscope has a different form factor than an endoscope, including different dimensional requirements. Furthermore, use of a laparascope involves at least one additional step of making an incision into a body so that the laparascope may be inserted into a body cavity. The laparoscope may be used with any of the imaging systems described above, and the imaging system 300 of FIG. 3 in particular would provide the benefit of a narrower bore for illumination and imaging optics.

It will further be appreciated that the imaging system 300 may be used to simplify imaging devices other than endoscopes and laparoscopes, such as by providing an integrated, coaxial illumination and image capture device using the techniques described above.

In addition to the surgical applications noted above in reference to FIG. 1, the endoscopic tool of FIG. 3 may be used for direct visualization of malignant or pre-malignant areas within a body cavity, or for image-guided placement of gene therapy and other medicinals to an area of interest within the body cavity.

Figure 4:
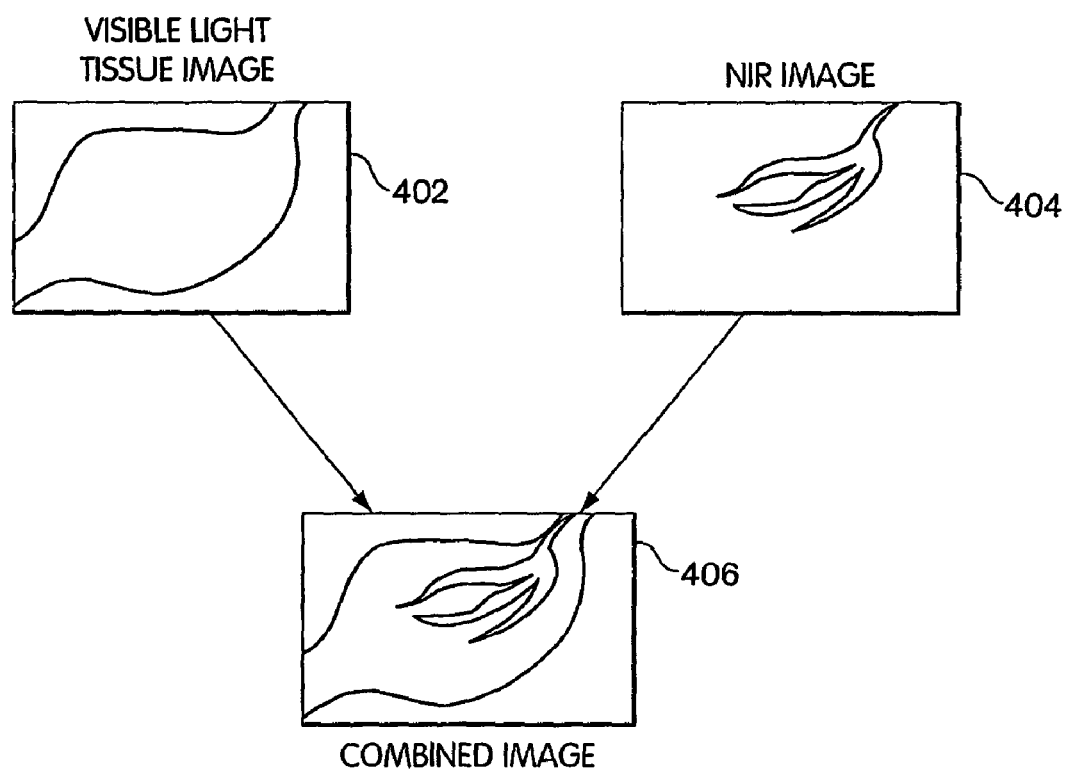
FIG. 4 shows an image displaying both a circulatory system and surrounding tissue.

FIG. 4 shows an image displaying both a circulatory system and surrounding tissue. As described above, a visible light tissue image 402 is captured of tissue within a surgical field. As noted above, the visible light tissue image 402 may include a subset of visible light wavelengths when an optical channel for dye imaging includes a wavelength within the visible light range. A near-infrared image 404 is also captured of the same (or an overlapping) field of view of the surgical field. Although referred to here for convenience as a near-infrared image, it should be clear that the dye-based image 404 may also, or instead, employ other wavelengths, such as far-red or infrared wavelengths. The near-infrared image 404 may be shifted to a visible wavelength for display, preferably using a color that is prominent when superimposed on the visible light tissue image 402. The images 402, 404 may be frame-rate adjusted as appropriate for video display of the surgical field.

The images may be displayed separately as the visible light tissue image 402 and the near-infrared image 404. Or the images 402, 404 may be combined into a combined image 406 by the image processing unit described above. The combined image 406 may then be used as an aid to the procedures described above, or to any other surgical or diagnostic procedure that might benefit from the dye-based imaging techniques described herein.

It will be appreciated that the above functionality is merely illustrative, and that other dyes, imaging hardware, and optics may be usefully deployed with the imaging systems described herein. For example, an endoscopic tool may employ a still-image imaging system for diagnostic photography within a body cavity. Or any of the imaging systems may be used as described above with excitation and/or emission wavelengths in the far-red spectrum. Through minor adaptations that would be clear to one of ordinary skill in the art, the system could be configured to image two or more functions (i.e., tumor and blood flow) at the same time that a visible light image is captured by associating each function with a different dye having a different emission wavelength. Non-medical applications exist for the imaging system. For example, dyes in a solution form may be sprayed on a mechanical component to identify oxidation, surface defects, or the like. Dyes could also be used to track gas, steam, or air flow through a pressurized system, and in particular to identify leaks around fittings and valves. These and other arrangements and adaptations of the subject matter discussed herein are intended to fall within the scope of the invention.

Thus, while the invention has been disclosed in connection with the preferred embodiments shown and described in detail, various modifications and improvements thereon will become readily apparent to those skilled in the art. It should be understood that all matter contained in the above description or shown in the accompanying drawings shall be interpreted as illustrative, and not in a limiting sense, and that the following claims should be interpreted in the broadest sense allowable by law.

The invention claimed is:

1. An imaging system for an open surgical procedure, the imaging system comprising:

a visible light source to illuminate a surgical field of a subject's body, the surgical field being exposed during the open surgical procedure, the visible light source providing a range of wavelengths including one or more wavelengths of visible light;

an excitation light source to illuminate the surgical field, the excitation light source including at least one wavelength outside the range of wavelengths of the visible light;

a lens disposed outside of the subject's body so as to receive at least a portion of reflected visible light from the surgical field and at least a portion of a fluorescence emission from the surgical field, the reflected visible light and the fluorescence emission propagating through free space outside of the subject's body from the surgical field to the lens, the lens providing focused reflected visible light and a focused fluorescence emission;

at least one electronic imaging device positioned with respect to the lens so as to capture a visible light image of the surgical field based on the focused reflected visible light, and a fluorescence emission image of the surgical field based on the focused fluorescence emission; and a display that renders a visual representation of the visible light image of the surgical field and the fluorescence emission image of the surgical field, the lens and the at least one electronic imaging device positioned outside of the subject's body, the positioning permitting performance of the open surgical procedure on the surgical field that includes at least an opening on an exterior surface of the subject's body where an open surgical procedure is being performed and, concurrently, illuminate the surgical field by the one or more wavelengths of visible light and the at least one wavelength outside the range of wavelengths of the visible light.

2. The system of claim 1 wherein the one or more wavelengths of visible light from the visible light source does not include far-red light, and wherein at least one of the at least one wavelength of the excitation light source and the emission wavelength includes a far-red light wavelength.

3. The system of claim 1 further comprising a filter that separates the focused fluorescence emission from the focused reflected visible light source, the focused fluorescence emission being directed toward a first optical transducer of the at least one electronic imaging device the focused reflected visible light being directed toward a second optical transducer of the at least one electronic imaging device.

4. The system of claim 3 wherein the second optical transducer separately senses at least each one of red, green, and blue light intensities.

5. The system of claim 3 wherein the second optical transducer separately senses at least each one of cyan, magenta, and yellow light intensities.

6. The system of claim 3 wherein the filter includes a dichroic mirror that reflects the focused fluorescence emission and transmits the focused reflected visible light.

7. The system of claim 3 wherein the filter includes a dichroic mirror that reflects the focused reflected visible light and transmits the focused fluorescence wavelength.

8. The system of claim 3 further comprising a second filter that shapes the focused reflected visible light.

9. The system of claim 1 wherein the at least one electronic imaging device includes at least one charge-coupled device.

10. The system claim 1 wherein the at least one electronic imaging device includes a video camera sensitive to the visible light.

11. The system of claim 1 wherein the at least one electronic imaging device includes an emission wavelength camera.

12. The system of claim 1 further comprising a processor that converts the fluorescence emission image to a converted image having one or more visible light components, and combines the converted image with the visible light image for display.

13. The system of claim 1 further comprising a processor that converts the fluorescence emission image to a converted image having one or more visible light components, and superimposes the converted image onto the visible light image for display.

14. The system of claim 1 wherein the visible light image is captured at thirty frames per second and the fluorescence emission image is captured at fifteen frames per second, the fluorescence emission image being converted to thirty frames per second for combination with the visible light image.

15. The system of claim 1 wherein the visible light image is captured at thirty frames per second and the fluorescence emission image is captured at fifteen frames per second, the visible light image being converted to fifteen frames per second for combination with the fluorescence emission image.

16. The system of claim 1 wherein the excitation light source includes a laser.

17. The system of claim 1 wherein:
the imaging system includes a surgical microscope; and
the display is constituted by a monocular or binocular eyepiece of the surgical microscope.

18. The imaging system of claim 1, wherein the visible light source further provides conventional lighting for the open surgical procedure.

19. The imaging system of claim 1, further comprising at least one of a hood, an enclosure, and a covering to provide an operating area for the open surgical procedure, wherein the operating area is closed to ambient light by the at least one of the hood, the enclosure and the covering.

20. A method for imaging an open surgical procedure, the method comprising:
A) performing the open surgical procedure on a surgical field with at least an opening on an exterior surface of the subject's body where the open surgical procedure is being performed, the surgical field being exposed during the open surgical procedure;
B.) positioning an imaging device outside of the subject's body to:
b1) concurrently with A), illuminate the surgical field with one or more wavelengths of visible light;
b2) concurrently with b1), illuminate the surgical field with at least one excitation wavelength that is not one of the one or more wavelengths of visible light;
C) introducing a fluorescent substance into the subject's body, the fluorescent substance emitting a fluorescence emission including at least one emission wavelength in response to the at least one excitation wavelength;
D) receiving, at a lens disposed outside of the subject's body, at least a portion of reflected visible light from the surgical field and at least a portion of the fluorescence emission from the surgical field, the reflected visible light and the fluorescence emission propagating through free space outside of the subject's body from the surgical field to the lens, the lens providing focused reflected visible light and a focused fluorescence emission;
E) electronically capturing a visible light image of the surgical field based on the focused reflected visible light;
F) electronically capturing a fluorescence emission image of the surgical field based on the focused fluorescence emission; and
G) displaying concurrently on a display device the visible light image and the fluorescence emission image.

21. The method of claim 20, wherein the surgical field includes a lesion, and wherein the fluorescent substance introduced in C) labels at least one of an antibody, an antibody fragment, and a low-molecular-weight ligand that accumulates at the lesion.

22. The method of claim 20, wherein the surgical field includes at, least a portion of the subject's circulatory system, wherein the fluorescent substance introduced in C) is soluble in blood, and wherein in F) and G), the fluorescence emission image includes a blood flow visualization of the portion of the subject's circulatory system in the surgical field.

23. The method of claim 20, wherein the fluorescent substance includes a fluorescent dye, and wherein C) comprises injecting the fluorescent dye into the patient's body by an intravenous injection.

24. The method of claim 20, wherein C) comprises spraying the fluorescent substance onto the surgical field.

25. The method of claim 20, wherein in C), the fluorescent substance includes one or more quantum dots.

26. The method of claim 20, wherein in C), the fluorescent substance includes at least one of indocyanine green, fluorescein, methylene blue, and IRDye78-CA.

27. The method of claim 20, wherein in C), the fluorescent substance is a dye having a structure of the formula:

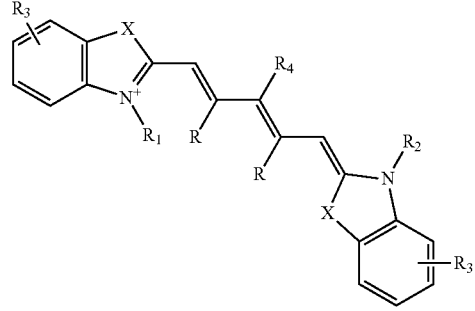

wherein, as valence and stability permit,
X represents $C(R)_2$, S, Se, O, or $NR_5$;
R represents H or lower alkyl, or two occurrences of R, taken together, form a ring together with the carbon atoms through which they are connected;
$R_1$ and $R_2$ represent, independently, substituted or unsubstituted lower alkyl, lower alkenyl, cycloalkyl, cycloalkylalkyl, aryl, or aralkyl;
$R_3$ represents, independently for each occurrence, one or more substituents to the ring to which it is attached;

$R_4$ represents H, halogen, or a substituted or unsubstituted ether or thioether of phenol or thiophenol; and $R_5$ represents, independently for each occurrence, substituted or unsubstituted lower alkyl, cycloalkyl, cycloalkylalkyl, aryl, or aralkyl.

28. The method of claim 20, wherein the subject is a patient.

* * * * *